(12) United States Patent
Gopalan et al.

(10) Patent No.: US 7,129,038 B2
(45) Date of Patent: Oct. 31, 2006

(54) METHOD FOR SELECTIVELY COMBINING MULTIPLE MEMBRANES FOR ASSEMBLY INTO TEST STRIPS

(75) Inventors: Ramanan Gopalan, Sunnyvale, CA (US); Jon Michael Messamer, San Jose, CA (US); Manoj Sharma, Milpitas, CA (US)

(73) Assignee: Lifescan, Inc., Milpitas, CA (US)

( * ) Notice: Subject to any disclaimer, the term of this patent is extended or adjusted under 35 U.S.C. 154(b) by 1018 days.

(21) Appl. No.: 10/177,542

(22) Filed: Jun. 21, 2002

(65) Prior Publication Data

US 2003/0235858 A1 Dec. 25, 2003

(51) Int. Cl.
*C12Q 1/00* (2006.01)

(52) U.S. Cl. .......................... 435/4; 422/56; 435/287.7; 435/287.8; 435/287.9; 435/805; 435/970; 436/169; 436/514; 436/810

(58) Field of Classification Search ..................... None
See application file for complete search history.

(56) References Cited

U.S. PATENT DOCUMENTS

| | | | | |
|---|---|---|---|---|
| 5,311,293 A | * | 5/1994 | MacFarlane et al. | 356/421 |
| 5,313,267 A | * | 5/1994 | MacFarlane et al. | 356/405 |
| 6,162,397 A | | 12/2000 | Jurik et al. | |

* cited by examiner

*Primary Examiner*—Christopher L. Chin

(57) ABSTRACT

A method for selectively combining multiple membranes for assembly into test strips (such as visual blood glucose test strips with side-by-side membranes). The method includes first measuring a plurality of color parameters (e.g., L*, a* and b*color parameters) associated with membrane samples from at least two membrane lots. Next, response characteristics (e.g., blood glucose response levels) are simulated for a speculative test strip that includes, for purposes of the simulation, combined multiple membranes tentatively selected from the at least two membrane lots. The simulated response characteristics are based on the measured plurality of color parameters of the tentative selection of combined multiple membranes. Optionally, the simulated response characteristics can also be based on simulated color parameters of the tentative selection of combined multiple membranes. Subsequently, assembly of the at least two membrane lots into a test strip with combined membranes is contingent on acceptable simulated response characteristics. Any suitable color parameters can be employed. The method can be used to selectively combine two or more membranes based on any number of color parameters. The assembled test strips can be used to measure glucose, cholesterol, proteins, ketones, phenylalanine or enzymes in blood, urine, saliva or other biological fluid, as well as sample fluid characteristics (e.g., pH and alkalinity).

16 Claims, 4 Drawing Sheets

METHOD FOR SELECTIVELY COMBINING MULTIPLE MEMBRANES FOR ASSEMBLY INTO TEST STRIPS

BACKGROUND OF THE INVENTION

1. Field of the Invention

This invention relates, in general, to methods for the manufacturing of test strips and, in particular, to methods for selectively combining multiple membranes for assembly into test strips.

2. Description of the Related Art

Various test strips have been developed for measuring the concentration of certain analytes in fluids and/or chemical properties of a fluid (e.g., pH or alkalinity). Such test strips can be used to measure, for example, glucose, cholesterol, proteins, ketones, phenylalanine or enzymes in blood, urine or saliva. These test strips frequently include multiple membranes that facilitate the determination of the analyte concentration or chemical property. For example, U.S. Pat. No. 6,162,397, which is fully incorporated herein by reference, describes a visual blood glucose test strip with two side-by-side membranes (i.e., paired membranes). Such paired membranes contain reagents which react with blood glucose to form visibly different colors (see also, Sherwood, M. et al., *A New Reagent Strip (Visidex™) for Determination of Glucose in Whole Blood*, Clinical Chemistry, 438–446 [1983]). A user can subsequently compare the two colors thus formed to a calibrated color chart (e.g., a color chart that includes sets of paired color pads) to ascertain blood glucose concentration.

FIG. 1 is a top plan view of a conventional visual blood glucose test strip 10. FIG. 2 depicts an exemplary calibrated color chart 200 for use with visual blood glucose test strip 10. Visual blood glucose test strip 10 includes a spreading top layer 12, an intermediate layer 14 with two membranes 14a and 14b (i.e., paired membranes 14a and 14b), and a support layer 16 with openings 16a and 16b. In operation, a user applies a blood sample to spreading top layer 12. As the blood sample penetrates spreading top layer 12, the blood sample spreads out and is substantially and uniformly distributed to paired membranes 14a and 14b. Glucose in the blood sample reacts with reagents in the paired membranes 14a, 14b, as it passes toward support layer 16, to form visually different colors in each of the paired membranes. The colors are viewed through openings 16a and 16b and compared with the paired color pads 202a–202h of calibrated color chart 200 to determine the blood glucose concentration of the blood sample. For the purpose of explanation only, calibrated color chart 200 in FIG. 2 is depicted to include eight sets of paired color pads (202a through 202h), each corresponding to one of eight targeted blood glucose test levels (e.g., 25, 50, 80, 120, 180, 240, 400 and 600 mg/dL). A user obtains a result by visually matching the paired membranes of a reacted visual blood glucose test strip to a paired set of color pads on calibrated color chart 200.

For quality assurance purposes during manufacturing, each lot of test strips with multiple membranes will customarily undergo acceptance testing in order to verify the accuracy of results obtained therewith. Such acceptance testing typically relies on any of a variety of standard color definition systems that specify color parameters for individual colors (for example, one of the color systems defined by the Commission Internationale de l'Eclairage (CIE) including the systems based on the L*a*b*color space and L*C*h color space). Methods for such acceptance testing are described in co-pending U.S. patent application Ser. No. 10/177,820 (tentatively identified by Attorney's Docket No. LFS-243 and incorporated herein by reference as if fully set forth) entitled "Acceptance Testing Method for Sets of Multiple Colored Workpieces."

The acceptance testing of a lot of test strips is conventionally conducted after multiple membranes (each from a separate lot of membranes) have been combined and assembled into the lot of test strips. However, a particular combination of multiple membranes that has been assembled into a lot of test strips may not be optimal or even acceptable in terms of result accuracy. If a lot of test strips undergoing acceptance testing does not meet acceptance criteria for result accuracy, the entire lot of test strips is subject to rejection.

Still needed in the field, therefore, is a method for selectively combining multiple membranes for assembly into a test strip that minimizes test strip lot rejection. In addition, the method should be objective and yet account for user-related visual effects.

SUMMARY OF INVENTION

The present invention provides a method for selectively combining multiple membranes for assembly into a test strip that minimizes test strip lot rejection during acceptance testing. The method is instrument-based and, therefore, objective, yet capable of accounting for user-related visual effects.

An method for selectively combining multiple membranes for assembly into a test strip according to one exemplary embodiment of the present invention includes first measuring a plurality of color parameters associated with membrane samples from at least two lots (a "first lot" and a "second lot") of membranes. Although the method is detailed below in terms of CIE L*a*b*color parameters and paired (i.e., two side-by-side) membranes of a visual blood glucose test strip for ease of description, once apprised of the present disclosure one skilled in the art will recognize that color parameters of other color systems can be employed and/or a different quantity of multiple membranes selectively combined for assembly into a test strip. For example, methods according to the present invention can be employed to selectively combine "m" multiple membranes for assembly into a test strip, where "m" is two or greater, based on "n" color parameters, where "n" can be any number.

It is also contemplated that methods in accordance with the present invention can be easily employed during the manufacturing of test strips with multiple membranes that are used to measure, for example, (i) glucose, cholesterol, proteins, ketones, phenylalanine or enzymes in blood, urine, saliva or other biological fluid and/or (ii) sample fluid characteristics such as pH and alkalinity.

Next, a response characteristic(s) of a speculative (i.e., hypothetical) test strip with multiple membranes is simulated. For purposes of the simulation, the speculative test strip includes a combination of multiple membranes that have been tentatively selected from the at least first lot of membranes and second lot of membranes. Furthermore, the simulated response characteristic(s) is based on the measured plurality of color parameters of the combined multiple membranes that have been tentatively selected. It should be noted that at this step of the method, the speculative test strip has not been physically assembled but is an imaginary construct for which the response characteristic(s), such as analyte concentration(s), are simulated.

The response characteristic of the speculative test strip that is simulated in methods according to the present invention can be any response characteristic known to one skilled in the art. Such a simulated response characteristic includes, but is not limited to, an analyte concentration of a biological fluid sample (e.g., a blood glucose concentration), a chemical property of a fluid sample (such as pH or alkalinity) and a statistical property (e.g., a measure of the variance or accuracy of the speculative test strip).

Next, the at least first and second lot of membranes, from which the combined multiple membranes were tentatively selected, is assembled into a test strip with combined multiple membranes. However, this assembly is contingent on an acceptable simulated response characteristic(s) for the speculative test strip that included the tentatively selected combined multiple membranes. If the simulated response characteristics are not acceptable, assembly of the multiple membranes into a test strip does not proceed and an alternative tentative selection of combined multiple membranes from another assortment of membrane lots can be made.

Since, in methods according to the present invention, multiple membranes are selectively combined for assembly into a test strip based on response characteristic(s) that are simulated prior to assembly, methods according to the present invention can optimize the performance characteristics (e.g., accuracy) of the assembled test strips and reduce test strip lot rejection during any subsequent acceptance testing. In addition, since the simulated response characteristic(s) are based on instrument-based measurements of color parameters, the methods are objective. Furthermore, algorithms that account for user-related visual effects can be employed during the simulation of the simulated response characteristic(s).

BRIEF DESCRIPTION OF DRAWINGS

A better understanding of the features and advantages of the present invention will be obtained by reference to the following detailed description that sets forth illustrative embodiments, in which the principles of the invention are utilized, and the accompanying drawings of which.

DETAILED DESCRIPTION OF THE INVENTION

Figure 3:
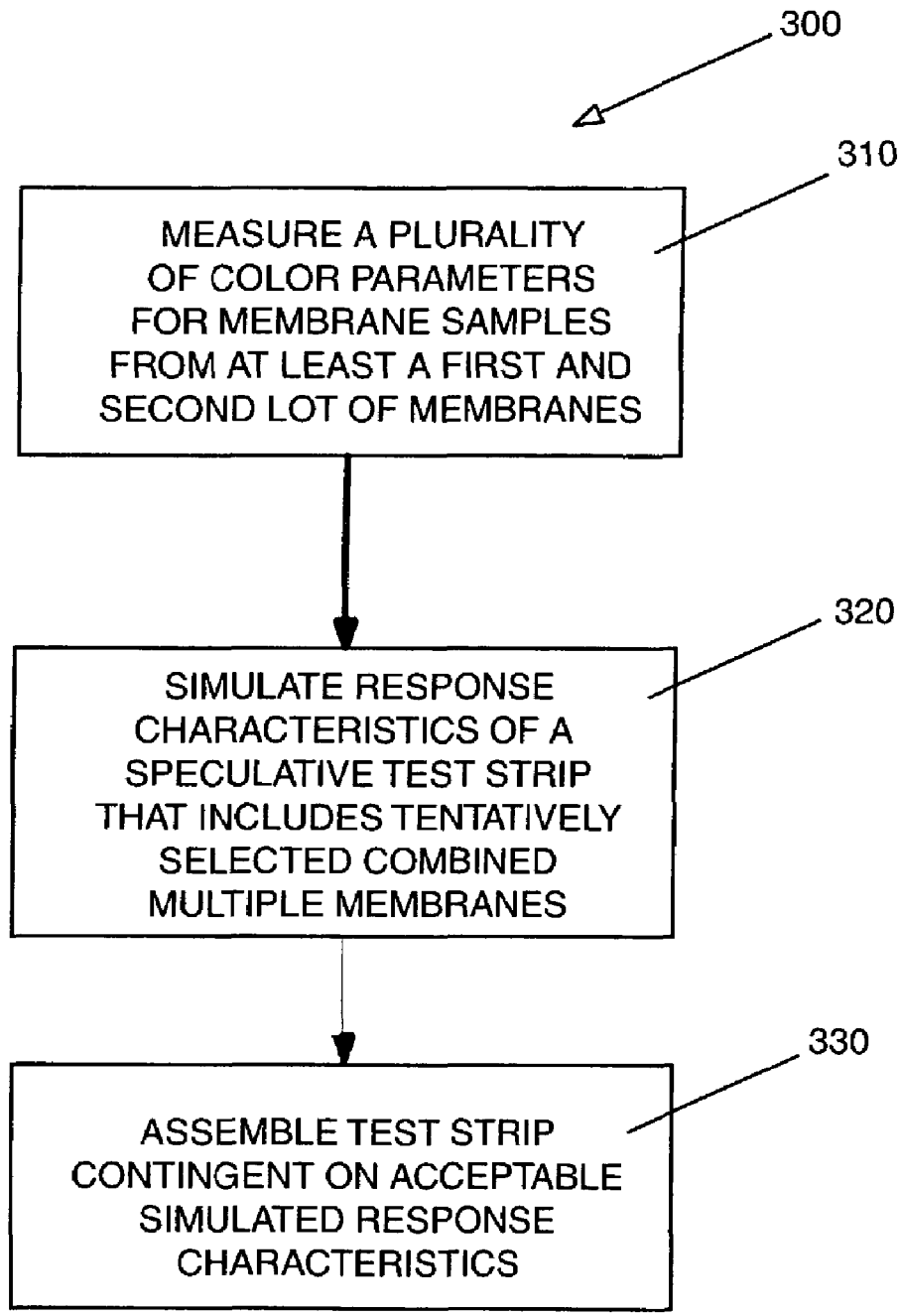
FIG. 3 is a flow diagram illustrating a sequence of steps in a process according to one exemplary embodiment of the present invention.

FIG. 3 is a flow diagram illustrating a sequence of steps in a process 300 for selectively combining multiple membranes for assembly into a test strip according to an exemplary embodiment of the present invention. Process 300 includes measuring a plurality of color parameters associated with membrane samples from at least two lots (i.e., a first lot and a second lot) of membranes, as set forth in step 310. The measuring of the color parameters can be accomplished using instruments and methods well known to one skilled in the art. For example, commercially available color parameter instruments such as a Minolta Chromameter model CR-241 (available from Minolta Co. Ltd, Osaka, Japan) or commercially available spectrophotometers can be employed to measure the color parameters.

The color parameters associated with the membrane samples include, but are not limited to, L*a*b*color parameters of the L*a*b*color space; X, Y and Z color parameters of the XYZ tristimulus space; Y, x and y color parameters of the Yxy color space; L*C*h*color parameters of the L*C*h*color space, and HL, a and b color parameters of the Hunter Lab color system. In the circumstance that L*a*b*color parameters are measured, the result of such a measurement will be three discrete color parameters for each of the membrane samples. For example, if there are two membrane samples (i.e., one membrane sampled from a first membrane lot and another membrane sampled from a second membrane lot) the result will be six discrete color parameters. Whereas, if there are three membrane samples, with each having been selected from one of three membrane lots, the result will be nine discrete color parameters. In general, for "q" membrane samples on which "n" color parameters are measured, the result will be q·n discrete color parameters.

Once apprised of the present disclosure, one skilled in the art will recognize that the membrane samples from the at least first and second membrane lots can take a variety of forms. For example, the membranes samples can include a plurality of membranes sampled from a first lot and a plurality of membranes sampled from a second lot, with each of the plurality of membranes from each lot having been reacted with a fluid sample containing a different concentration of analyte. Furthermore, methods in accordance with the present invention can be easily employed during the manufacturing of test strips with multiple membranes that are used to measure, for example, (i) the level of glucose, cholesterol, proteins, ketones, phenylalanine or enzymes in blood, urine, saliva or other biological fluid and/or (ii) sample fluid characteristics such as pH and alkalinity.

Next, as set forth in step 320, response characteristics of a speculative test strip are simulated. The speculative test strip includes, for purposes of simulating the response characteristics, combined multiple membranes tentatively selected from the at least first and second lots of membranes. In addition, the simulated response characteristics are based on the measured plurality of color parameters from step 310.

It is contemplated that the combined multiple membranes that are tentatively selected at step 320 can originate from a sub-set of the lots from which membrane samples were measured at step 310. For example, if membrane samples from 10 lots were measured, then the "combined multiple membranes" for a speculative test strip with two membranes will be tentatively selected from only a two lot sub-set of the 10 lots. Similarly, for a speculative test strip with m membranes, the "combined multiple membranes" will be tentatively selected from an m lot sub-set of the lots from which membrane samples were measured.

The response characteristics of the speculative test strip can be simulated, for example, utilizing an algorithm that relates a response characteristic (P) to the color parameters ($CP_1$ to $CP_{m \cdot n}$). In general, such an algorithm takes the form of equation (1) below:

$$P = f(CP_1, CP_2, \ldots CP_{m \cdot n}) \quad (1)$$

where: P is the response characteristic; and
$CP_1, CP_2 \ldots CP_{m \cdot n}$ are the m·n color parameters associated with the m selected multiple membranes.

Equation (1) essentially converts the color parameters of the selected multiple membranes into a simulated response characteristic (e.g., a simulated analyte concentration) that would be produced by the speculative test strip that includes those multiple membranes.

In order to more accurately simulate response characteristics of a speculative test strip, by taking into account fixed, random and residual sources of variability associated with sampling and the test method employed for measurement of color parameters, it can be beneficial to optionally simulate response characteristics based not only on the measured color parameters but also based on color parameters that are themselves simulated (i.e., simulated color parameters). The simulated color parameters can be simulated (obtained) using, for example, an experimentally-derived multivariate mixed model equation of the general form:

$$R = Y\beta + Z\gamma + e \quad (2)$$

where:

R is an N×1 vector of color parameters $\beta$ is a b×1 vector of fixed effect coefficients Y is an N×b matrix of independent covariates $\gamma$ is a g×1 vector of random effect coefficients Z is an N×g matrix of random effects; and e is an N×1 vector of residual errors.

In order to effectively increase the distribution of simulated response characteristics for the speculative test strip, it can be beneficial to optionally simulate response values that are intermediate to those of measured color parameters: This can be accomplished, for example, by fitting a linear regression model to the simulated response characteristic(s) with a reference response characteristic(s) as an independent variable. Such a linear regression model has the general form:

$$\text{Simulated response characteristic} = A^*(\text{reference response characteristic}) + B + e \quad (3)$$

where:

A is the slope of the linear regression

B is the intercept of the linear regression; and e is an error term.

Furthermore, to account for user-related visual effects, it can be optionally beneficial to estimate the variance of the simulated response characteristics and to adjust the variance to account for the user-related visual effects. The variances of the simulated response characteristics can be subsequently computed at each level of the reference response characteristic. To adjust for a larger variation due to any user-related visual effects, the standard deviation of the simulated response characteristic can then be multiplied by an inflation factor. This can be accomplished using the standard normal deviate, as follows:

$$\text{Predicted analyte level} = A^*(\text{reference analyte value}) + B + \epsilon$$

Where, for reference response values associated with measured color parameters:

$$\epsilon = N(0,1)^*\text{inflation factor}^*Sqrt(\text{test level variance})$$

and where, for reference response values associated with simulated color parameters that are intermediate to those of measured color parameters:

$$\epsilon = N(0,1)^*\text{inflation factor}^*Sqrt(0.5^*(V1+V3))$$

where:

V1 is the variance for the lower values, associated with measured color parameters, bracketing the intermediate level V3 is the variance for the higher values, associated with measured color parameters, bracketing the intermediate level, and N(0,1) is a standard normal deviate.

After the response characteristics have been simulated, the at least first and second lot of membranes, from which the tentatively combined multiple membranes were sampled, are assembled into a test strip with combined membranes. The assembly is, however, contingent on the simulated response characteristics being acceptable, as set forth in step 330. The acceptability of the simulated response characteristics can be determined based on comparison to a specification(s) and/or any known method of assessing the accuracy of the simulated response characteristics such as a Clarke's Error Grid analysis.

A Clark's Error Grid analysis provides a method to assess the clinical accuracy of a blood glucose monitoring device (e.g., a visual blood glucose test strip). The error grid of such an analysis categorizes a device's response against a reference value into one of five clinical accuracy zones (i.e., zones A–E). Where zone A indicates clinically accurate results; zone B indicates results that are not clinically accurate but pose minimal risk to patient health; and zones C through E indicate clinically inaccurate results that pose increasing potential risk to patient health (see Clarke, William L. et al., Evaluating Clinical Accuracy of Systems for Self-Monitoring of Blood Glucose, Diabetes Care, Vol. 10 No. 5, 622–628 [1987]). Specifications can be developed based on the proportion of results falling within the various error grid zones or more rigorously, the lower confidence bound of the proportion (e.g., the lower 90% Confidence Limit for the proportion of data points in Zone A+Zone B is at least 0.90 or greater).

Those skilled in the art will appreciate that methods according the present invention can be beneficially employed to select a combination of multiple membranes for assembly into a test strip by measuring the color parameters of membranes sampled from a plurality of membrane lots and then choosing only those combinations of multiple membranes that provide for a test strip of acceptable accuracy for assembly into a test strip. Therefore, this method optimizes the accuracy of the assembled test strips.

Figure 1:
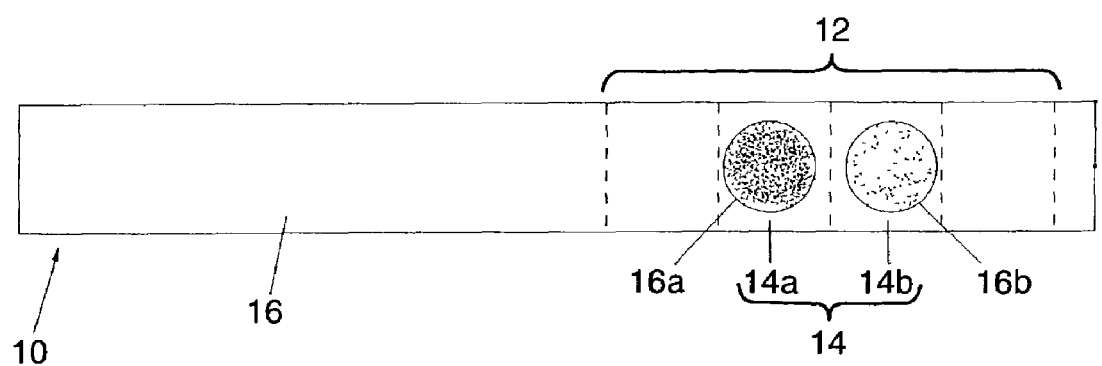
FIG. 1 is a bottom plan view of a conventional visual blood glucose test strip.
Figure 2:
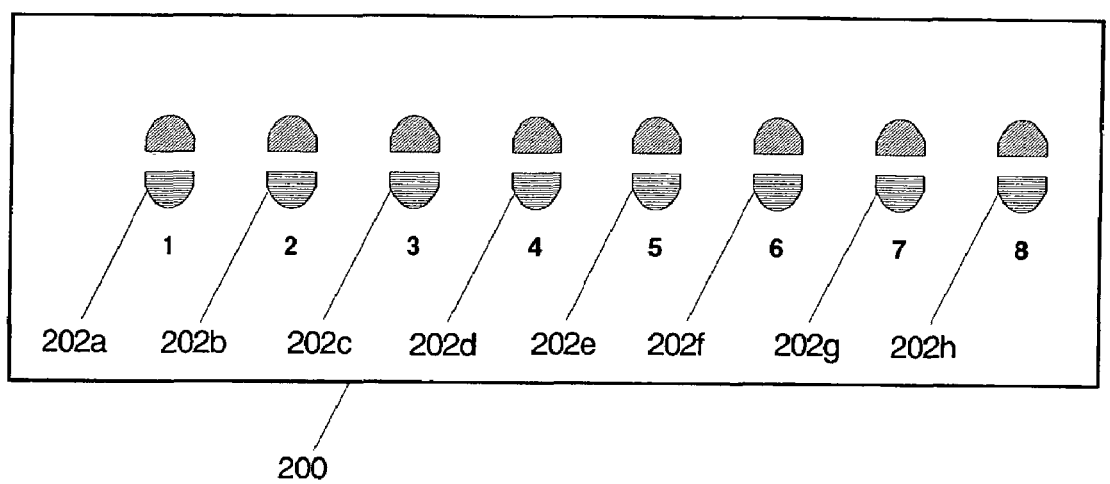
FIG. 2 is a simplified top plan view of an exemplary calibrated color chart as may be used in conjunction with the conventional visual blood glucose test strip of FIG. 1.
Figure 4:
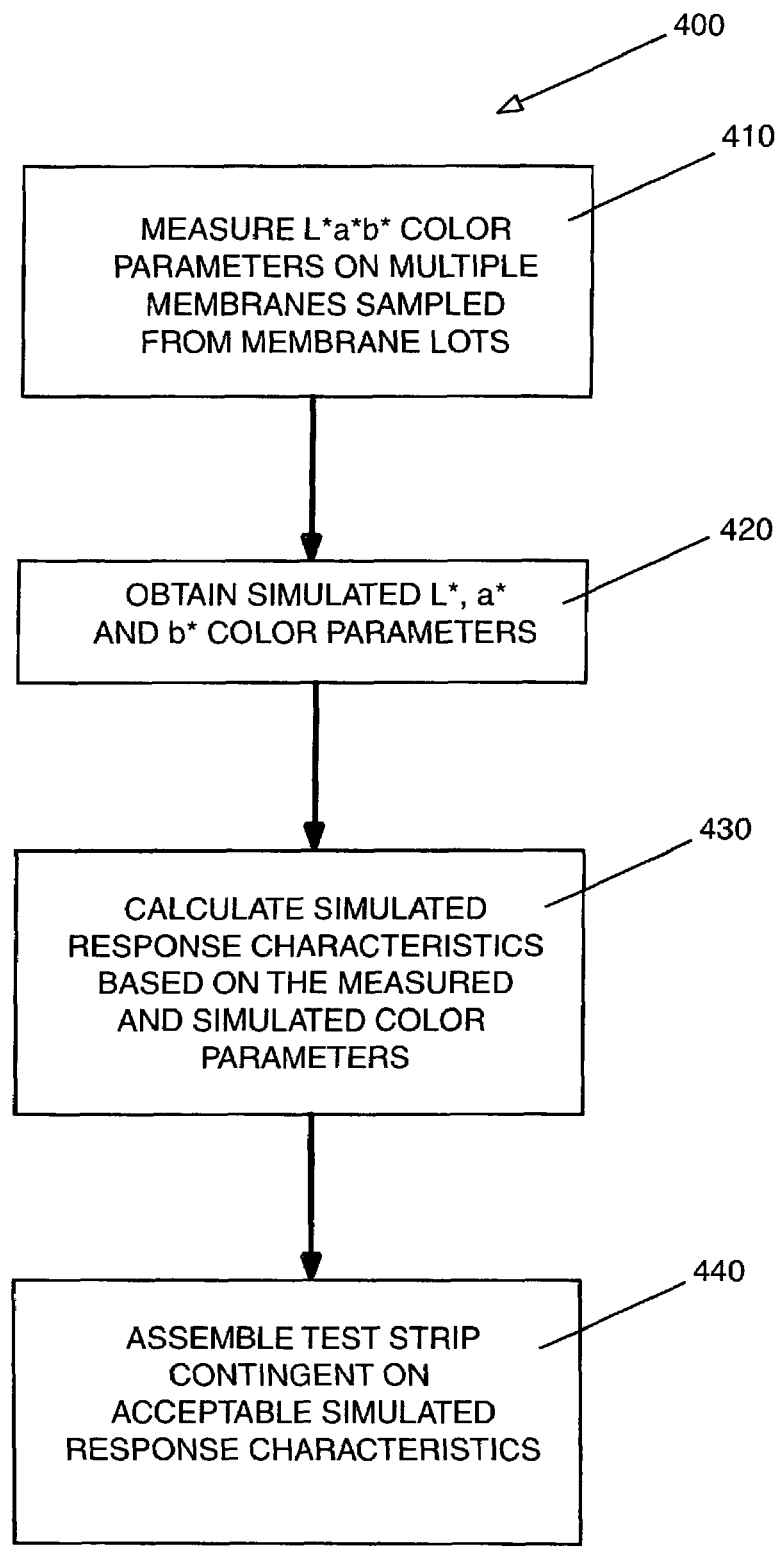
FIG. 4 is a flow diagram illustrating a sequence of step in a process according to another exemplary embodiment of the present invention.

Exemplary Method for the Selective Combining of Two Membranes for Assembly into a Visual Blood Glucose Test Strip Referring to FIGS. 1 and 4, a process 400 that was developed for selectively combining two membranes into a visual blood glucose test strip 10 is described. The side-by-side membranes of such a visual blood glucose test strip can be manufactured, for example, using well known web-based process in which tracks are a source of variation.

Three color parameters (i.e., L*, a* and b*color parameters) were measured on multiple (i.e., twelve) membranes, with six of the twelve membranes having been sampled from a first lot of membranes (i.e., a "blue membrane" lot) and the other six of the twelve having been sampled from a second lot of membranes (i.e., a "yellow" membrane lot), using a Minolta Chromameter. See step 410. Prior to measurement, the membrane samples from each of the blue and yellow membrane lots were reacted with blood glucose at a level of either 50, 80, 120, 180, 270 or 400 mg/dL.

Using the following linear mixed model derived from Equation (2) above, simulated L*, a* and b*color parameters were obtained for tested blood glucose levels of 50, 80, 120, 180, 270 or 400 mg/dL (see step 420).

$$r_{ijkl} = \alpha_i + \beta_i * Y_{ijkl} + b_j + t_k + e_{ijkl}$$

where:

i=1, 2, . . . , 6 (the number of glucose levels used to derive the linear mixed model);

j=1, 2, . . . , 4 (the number of different types of blood used to derive the linear mixed model);

k=1, 2, . . . , 4 (the number of tracks used in manufacturing test strips);

l=1, 2, . . . , 4 (the number of replicates tested to derive the linear mixed model);

$b_j \sim N(0,\sigma_B^2)$, $t_k \sim N(0, \sigma_T^2)$ and $e_{ijkl} \sim N(0, \sigma^2)$;

$r_{ijkl}$ is any one of the L*, a* and B*color parameters, $\alpha$ is an intercept of the linear mixed model, $\beta$ is a slope of the linear mixed model $Y_{ijkl}$ is an average reference instrument analyte value at a particular glucose level; and $\sigma_B^2$, $\sigma_T^2$ and $\sigma^2$ are the variances for blood, track and residual, respectively.

The coefficients of the above equation are unique to a manufactured membrane at each tested reference analyte level and vary by membrane lot and manufacturing run. The coefficient values can be, for example, experimentally derived from measured color parameter data.

Next, as set forth in step 430, simulated response characteristics (i.e., simulated blood glucose level responses) were calculated from the simulated color parameters using the following equation that was derived from Equation (1):

$$R = (28.874823 - 0.245112*blueL - 0.178014*yellL -$$
$$0.392156*yellb + 0.011033*bluea^2 + 0.003151*yellb^2 +$$
$$0.003091*yellL*blueL - 0.002856*yella*yellb -$$
$$0.004318*yellb*blueb)^2$$

While this example illustrates the use of simulated color parameters for simulating response characteristics, one skilled in the art will recognize that measured color parameters and/or simulated color parameters can be utilized to simulate response characteristics of a speculative test strip.

Since an objective of process 400 is the selection of multiple membranes for assembly into a visual blood glucose test strip, it was desirable to estimate the variability of the simulated response characteristics and to adjust that variability to account for user-related visual effects (e.g., the additional variability associated with a user's visual comparison of a visual blood glucose test strip to a calibrated color chart). This was accomplished through the use of a linear regression model (derived from equation (3)) that used the simulated response characteristic (i.e., simulated glucose level) as a response and reference measurements as the independent variable. The resulting equation was:

Simulated glucose value=intercept+slope*(average reference measurement)+e where "e" is an error term calculated using the standard normal deviate as follows:

| Glucose Point | e |
|---|---|
| 50 | N(0,1)* 1.5*Sqrt(V50) |
| 65 | N(0,1)* 1.5*Sqrt(0.5*(V50 + V80)) |
| 80 | N(0,1)* 1.5*Sqrt(V80) |
| 100 | N(0,1)* 1.5*Sqrt(0.5*(V80 + V120)) |
| 120 | N(0,1)* 1.5*Sqrt(V120) |
| 150 | N(0,1)* 1.5*Sqrt(0.5*(V120 + V180)) |
| 180 | N(0,1)* 1.5*Sqrt(V180) |
| 225 | N(0,1)* 1.5*Sqrt(0.5*(V180 + V270)) |
| 270 | N(0,1)* 1.5*Sqrt(V270) |
| 335 | N(0,1)* 1.5*Sqrt(0.5*(V270 + V400)) |
| 400 | N(0,1)* 1.5*Sqrt(V400) | and where N(0,1) is a standard normal deviate.

The coefficients of the equations are unique to a specific pairing of manufactured membrane lots and vary by membrane lot and manufacturing run. The coefficient values are experimentally derived from measured color parameter data.

Next, as set forth in step 440, a Clarke's Error Grid analysis was performed on the simulated response characteristics to determine the acceptability thereof. Contingent on the acceptability of the simulated response characteristics, a test strip with multiple membranes was assembled.

It should be understood that the various alternatives to the embodiments of the invention described herein may be employed in practicing the invention. It is intended that the following claims define the scope of the invention and that methods within the scope of these claims and their equivalents be covered thereby.

What is claimed is:

1. A method for selectively combining multiple membranes for assembly into test strips comprising:

measuring a plurality of color parameters associated with membrane samples from at least a first lot of membranes and a second lot of membranes;

simulating response characteristics of a speculative test strip that includes, for purposes of simulating the response characteristics, combined multiple membranes tentatively selected from the at least first lot of membranes and second lot of membranes, the simulated response characteristics being based on the measured plurality of color parameters of the tentative selection of combined multiple membranes, wherein the simulated response characteristics are also based on simulated color response data and are obtained utilizing an experimentally-derived multivariate mixed model equation of the form:

$$R = Y\beta + Z\gamma + e$$

where:

R is an N×1 vector of color parameter responses;

$\beta$ is a b×1 vector of fixed effect coefficients;

Y is an N×b matrix of independent covariates;

$\gamma$ is a g×1 vector of random effect coefficients;

Z is an N×g matrix of random effects; and e is a N×1 vector of residual errors; and assembling the at least first and second lot of membranes from which the combined multiple membranes were tentatively selected into a test strip with combined membranes, the assembly contingent on an assessment of acceptable test strip clinical accuracy based on the simulated response characteristics.

2. The method of claim 1, wherein the simulating step further includes estimating the variances of the simulated response characteristics and adjusting the variances for user-related visual effects.

3. The method of claim 1, wherein the assembling step includes assembly contingent on an assessment of acceptable test strip clinical accuracy based on the simulated response characteristics as determined by comparison of the simulated response characteristics to a specification indicative of test strip of acceptable clinical accuracy.

4. The method of claim 1, wherein the assembling step includes assembly contingent on an assessment of acceptable test strip clinical accuracy based on the simulated response characteristics as determined using a Clarke's Error Grid analysis.

5. The method of claim 1, wherein the measuring step measures L*, a* and b*color parameters of the L*a*b*color space of the Commission Internationale de L'Eclairage.

6. The method of claim 1, wherein the measuring step is accomplished using a chromameter.

7. The method of claim 1, wherein the measuring step is accomplished using a spectrophotometer.

8. The method of claim 1, wherein the measuring step measures X, Y and Z color parameters of the XYZ tristimulus space.

9. The method of claim 1, wherein the measuring step measures Y, x and y values of the Yxy color space.

10. The method of claim 1, wherein the measuring step measures L, C and h values of the L*C*h color space Commission Internationale de L'Eclairage.

11. The method of claim 1, wherein the measuring step measures HL, a and b values of the Hunter Lab color system.

12. The method of claim 1, wherein the measuring step includes measuring a plurality of color parameters on membrane samples that have been reacted with an analyte.

13. A method for selectively combining multiple membranes for assembly into visual test strips, the visual test strips for use in determination of analyte concentration in a biological fluid, the method comprising:

measuring L*, a* and b*color parameters, Commission of the Internationale de L'Eclairage, associated with membrane samples from at least a first lot of membranes and a second lot of membranes;

obtaining simulated color parameters associated with the membrane samples selected from at least the first lot of membranes and the second lot of membranes;

simulating response characteristics of a speculative test strip that includes, for purposes of simulating the response characteristics, combined multiple membranes tentatively selected from the at least first lot of membranes and second lot of membranes, the simulated response characteristics being based on the measured plurality of color parameters and the simulated color parameters of the tentative selection of combined multiple membranes, wherein the simulated response characteristics are also based on simulated color response data and are obtained utilizing an experimentally-derived multivariate mixed model equation of the form:

$R = Y\beta + Z\gamma + e$ where:

R is an N×1 vector of color parameter responses;

β is a b×1 vector of fixed effect coefficients;

Y is an N×b matrix of independent covariates;

γ is a g×1 vector of random effect coefficients;

Z is an N×g matrix of random effects; and e is a N×l vector of residual errors; and assembling the at least first and second lot of membranes into a test strip with combined membranes contingent on an assessment of acceptable test strip clinical accuracy based on the simulated response characteristics.

14. The method of claim 13, wherein the simulating step further includes estimating the variances of the simulated response characteristics and adjusting the variances for user-related visual effects.

15. The method of claim 13, wherein the assembling step includes assembly contingent on an assessment of acceptable test strip clinical accuracy based on the simulated response characteristics as determined by comparison of the simulated response characteristics to a specification indicative of a test strip of acceptable clinical accuracy.

16. The method of claim 13, wherein the assembling step includes assembly contingent on an assessment of acceptable test strip clinical accuracy based on the simulated response characteristics as determined using a Clarke's Error Grid analysis.

* * * * *